United States Patent [19]

Lasser et al.

[11] Patent Number: 5,514,125

[45] Date of Patent: May 7, 1996

[54] APPLICATOR FOR THE TREATMENT OF AN ELEVATED INTERNAL OCULAR PRESSURE BY MEANS OF LASER RADIATION

[75] Inventors: Theo Lasser; Peter Schäffer, both of Oberkochen; Peter Reimer, Ellwangen; Klaus Gottwaldt; Joachim Hug, both of Oberkochen, all of Germany

[73] Assignee: Carl-Zeiss-Stiftung, Heidenheim (Brenz), Germany

[21] Appl. No.: 370,126

[22] Filed: Jan. 9, 1995

[30] Foreign Application Priority Data

Jun. 17, 1994 [DE] Germany ........................ 9409616 U

[51] Int. Cl.⁶ .................................................. A61B 17/36
[52] U.S. Cl. .................................... 606/4; 606/16; 606/17
[58] Field of Search ................................ 606/10, 11, 12, 606/14, 15, 16, 17

[56] References Cited

U.S. PATENT DOCUMENTS

| | | | |
|---|---|---|---|
| 4,736,743 | 4/1988 | Daikuzono | 606/15 |
| 5,078,711 | 1/1992 | Kakami et al. | 606/15 |
| 5,146,917 | 9/1992 | Wagnieres et al. | 606/15 |
| 5,190,536 | 3/1993 | Wood et al. | 606/17 |
| 5,207,673 | 5/1993 | Ebling et al. | 606/15 |
| 5,348,552 | 9/1994 | Nakajima et al. | 606/28 |

*Primary Examiner*—Angela D. Sykes
*Assistant Examiner*—Sonya Harris-Ogugua

[57] ABSTRACT

An applicator for treatment of an elevated internal ocular pressure by means of laser radiation has a handpiece, which releasably surrounds a fiber optic light guide on its exit side end. A sleeve portion is releasably connected to the exit side end of the light guide, a condensing optical element being provided in the sleeve portion, optically dimensioned and arranged in the sleeve portion at a distance from the exit side end of the light guide such that the applied laser radiation can be focused in the ciliary body of the eye on contact of the sleeve portion with the surface of the eye.

15 Claims, 1 Drawing Sheet

APPLICATOR FOR THE TREATMENT OF AN ELEVATED INTERNAL OCULAR PRESSURE BY MEANS OF LASER RADIATION

BACKGROUND OF THE INVENTION

1. Field of the Invention

The present invention relates to an applicator for the treatment of an elevated internal ocular pressure by means of laser radiation.

An elevated internal ocular pressure, usually termed glaucoma, can be reduced by the coagulation of the ciliary body of the eye by irradiation with laser radiation of a suitable wavelength. A description of this method was, for example, given by D. E. Gaasterland et al. The abstract of his lectures can be found in Invest. Opththalmol. and Visual Sci., Vol. 33, 1992, pp. 1644, entitled "A Multicenter Study of Contact Diode Laser Transscleral Cyclophoto-Coagulation in Glaucoma Patients."

2. Relevant Prior Art

A suitable applicator for carrying out this process is furthermore known from the International Patent Application WO 92/16259. The applicator described there includes a sleeve which has a tapered shape on the exit side, approximately matching the surface of the eye. The end of the fiber optic light conductor arranged in the applicator is arranged at a certain distance from the application surface. Due to the divergent light guide radiating characteristic, problems in bringing the applied laser power to act fully on the ciliary body arise because of this arrangement. Furthermore there exists the danger of not only irradiating the ciliary body but also damaging surrounding tissues in the eye.

In the case of an arrangement in which the exit end of the fiber optic light conductor is brought into direct contact with the surface of the eye, i.e. with the conjunctiva, problems likewise arise. Because of the high power density in the boundary surface, adhesion of the fiber to the conjunctiva can occur there, which likewise represents a danger for the patient.

SUMMARY OF THE INVENTION

The object of the present invention is therefore to provide an applicator for the treatment of an elevated internal ocular pressure by means of laser radiation, which makes possible an application of laser radiation into the ciliary body which is safe for the patient. Furthermore a simpler construction and also as comfortable as possible an access with the applicator are required.

This object is achieved by an applicator according to the invention, having a handpiece, which releasably surrounds a fiber optic light guide on its exit side end. A sleeve portion is releasably connected to the exit side end of the light guide, a condensing optical element being provided in the sleeve portion, optically dimensioned and arranged in the sleeve portion at a distance from the exit side end of the light guide such that the applied laser radiation can be focused in the ciliary body of the eye on contact of the sleeve portion with the surface of the eye.

A complete apparatus for the treatment of an elevated internal eye pressure by means of laser irradiation combines a diode laser and the applicator according to the invention including a fiber optic light guide.

According to the invention, the applicator has a handpiece which releasably surrounds a fiber optic light guide on the exit side. Furthermore, a sleeve portion is provided which is releasably connected to the fiber optic light guide and which contains a condensing optical element. This, furthermore, is dimensioned, or arranged in the sleeve portion, such that the applied laser radiation is focused into the ciliary body of the eye on contact of the sleeve portion with the surface of the eye.

Because of the separation of the applicator into the individual components, for one thing a simpler construction results, making possible an optimization of all the individual components per se.

The spacing of the condensing optical element provided in the sleeve portion from the exit surface of the light guide moreover brings about a reduced power density at the boundary surface between the surface of the eye and the abutting optical element. Adhesion of the applicator to the conjunctiva is thus prevented.

The condensing optical element in the sleeve portion moreover counteracts the scattering effect of the sclera in the eye. The consequence is that the applied radiation reaches the ciliary body practically completely, and thus the probability of damaging the surrounding portions of the eye is reduced.

Advantageously, it has been found that it is possible to produce the sleeve portion at a favorable cost by an extrusion process. Here it is even possible to produce the complete sleeve portion as a single extruded part, i.e., thus also the surface of the optical element. Since the sleeve portion, as a single part, has direct contact with the surface of the eye, only the sleeve portion has to be sterilized, which is ensured by a suitable choice of material.

It is further possible to keep in readiness varied sleeve portions with different optical elements of different optical effect, which can be individually used according to the eye to be treated.

BRIEF DESCRIPTION OF THE DRAWINGS

Further advantages, and also details of the applicator according to the invention, will become apparent from the following description of preferred embodiments with reference to the accompanying figures.

FIG. 2b shows a transverse sectional representation of the handpiece of FIGS. 1 and 2a;

DETAILED DESCRIPTION OF PREFERRED EMBODIMENTS

Figure 1:
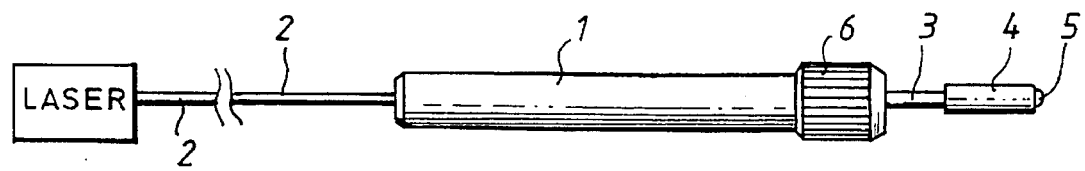
FIG. 1 shows a side view of an embodiment of the complete mounted applicator.

A side view is shown in FIG. 1 of an embodiment of the complete mounted applicator according to the invention. The applicator according to the invention comprises an essentially cylindrical handpiece (1) into which the fiber optic light guide (2), coupled to a laser, is introduced centrally. Here the fiber optic light guide is surrounded over a given length on the exit side by a rigid end sleeve (3). The end sleeve ends on the exit side flush with the fiber optic light guide (2) guided in it, and projects a little over the exit side end of the handpiece (1). In the embodiment shown, an end sleeve (3) made of light metal is provided for the fiber optic light guide (2).

In the applicator according to the invention, a sleeve portion (4) is now slipped onto the projecting end of the end sleeve (3) including the fiber optic light guide (2) located therein. The sleeve portion (4) is likewise of cylindrical construction and has a corresponding diameter which makes possible the releasable slipping of the sleeve portion (4) onto the end sleeve (3) of the fiber optic light guide (2). A releasable connection between the fiber optic light guide (2) or the end sleeve (3) and the sleeve portion (4) is thereby realized. On the exit side, a condensing optical element (5) is arranged in the sleeve portion (4); it is only partially visible in FIG. 1.

The end sleeve (3) or the fiber optic light guide (2) is secured in the radial and axial direction in the handpiece (1) by means of a securing element (6) which can be screwed onto the exit side. The securing element (6) is designed as a cap nut in the embodiment example shown, and is screwed onto a corresponding thread of the handpiece (1).

The design of the applicator according to the invention now makes it possible for the respective user to allow the end sleeve (3) of the fiber optic light guide to project to a desired extent beyond the end surface of the handpiece (1). An individual setting of the distance between the handpiece (1) and the contact surface on the eye, that is, a variable setting of the working distance, is thereby possible.

Figure 2A:
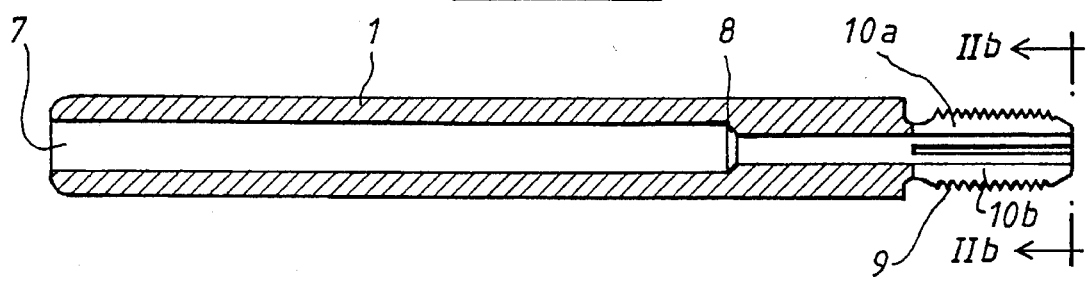
FIG. 2a shows a longitudinal sectional representation of the handpiece of the embodiment of FIG. 1.

FIG. 2a shows a longitudinal sectional representation of the handpiece of FIG. 1. The cylindrical handpiece (1) has an internal cylindrical bore (7) into which the fiber optic light guide (2), or the end sleeve (3), can be introduced. A narrowed bore diameter, conforming to the outer diameter of the end sleeve, is provided in the cylindrical bore (7) at a defined distance in front of the exit side end of the handpiece (1), and by means of it the end sleeve (3) and thus the light guide is centered in the distal (exit side) region.

The handpiece (1) furthermore has on the exit side a securing device for the fiber optic light guide to be introduced or for the end sleeve, and is constructed on the principle of a collet chuck. For this purpose, the handpiece has four slots over the cylinder periphery so that four securing jaws (10a, 10b) result, which surround the introduced end sleeve in a frictional engagement. Only two of the four securing jaws are visible in the representation of FIG. 2a. A suitable thread (9), onto which the securing element in the form of a suitable cap nut can be screwed, is moreover provided on the outside of the handpiece. The four securing jaws are conical in the distal region and cooperate with a corresponding conical surface of the screwed-on securing element, such that the fiber optic light guide or the end sleeve is precisely fixed in the handpiece (1) and the desired working distance can be set in a defined manner. Aluminum, stainless steel, or hard plastics have been found to be suitable materials for the handpiece.

Figure 2B:
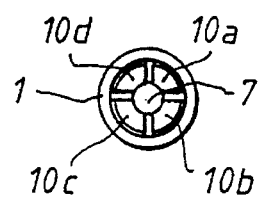

FIG. 2b shows a cross section of the handpiece (1) through the plane of the collet chuck securing device shown in FIG. 2a. The four securing jaws (10a, 10b, 10c, 10d) of the securing device, which are separated by the slots present between them, are arranged around the bore (7) which runs centrally and into which the fiber optic light guide or the end sleeve is introduced. The desired secure fixing of the fiber optic light guide or of the closure sleeve is ensured by a suitable dimensioning of the diameter of the central bore.

Figure 3:
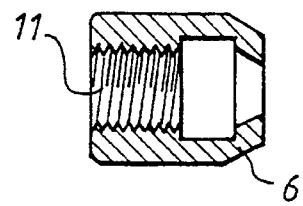
FIG. 3 shows a cross sectional representation of the securing element which can be screwed onto the handpiece.

A cross sectional representation of the securing element (6) which can be screwed onto the clamp jaw securing device of the handpiece (1) is shown in FIG. 3. Clearly visible here is the fitting internal thread (11) within the securing element (6), with which it is screwed onto the exit side end of the applicator and securely fixes the fiber optic light guide or its end sleeve. The securing element (6), constructed as a cap nut, of the embodiment example shown, is here likewise made of aluminum, hard plastic, or stainless steel.

Figure 4A:
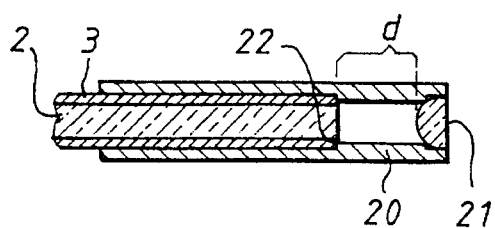
FIG. 4a shows a longitudinal sectional representation of a first embodiment of the sleeve portion.
Figure 4B:
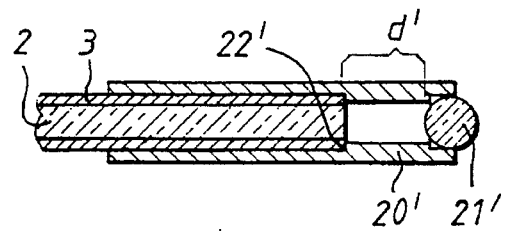
FIG. 4b shows a longitudinal sectional view of a second embodiment of the sleeve portion.

Two embodiments of possible designs of the sleeve portion (4) of FIG. 1, which can be slipped onto the end sleeve, will now be explained with reference to FIGS. 4a and 4b. In FIGS. 4a and 4b, the respective exit side end of the end sleeve (3), including the fiber optic light guide (2) located therein, and onto which a respective sleeve portion (20, 20') is slipped, is shown in section. The respective sleeve portion has for this purpose an internal diameter corresponding to the external diameter of the end sleeve (3). In the embodiment shown in FIG. 4a, a plano-convex lens is now arranged on the exit side as the condensing optical element (21). This is optically dimensioned, and also arranged in such a manner in the sleeve portion, such that the thus applied laser radiation, on contact with the plano-convex lens, is in fact focused onto the ciliary body of the eye. In the dimensioning or arrangement of the optical element (21), the starting point is that the fiber optic light guide (2), or its exit surface, terminates flush with the end sleeve (3). The sleeve portion (20) has a corresponding annular shoulder (22) in the interior as a stop surface for the precise positional arrangement of the sleeve portion (20) on the end sleeve (3), to ensure a defined and reproducible relative position between the condensing optical element (21) and the light guide exit surface. The distance (d) between the light guide exit surface and the convex boundary surface of the plano-convex lens used is decisive here. The plano-convex lens is preferably made of KF9 glass and has a radius of curvature of the convex surface of 0.5 to 3 mm, preferably r=1.527 mm, while the distance is four times the radius of curvature, and thus 2–12 mm, preferably d=6 mm.

A second embodiment of the sleeve portion (20') is shown in section in FIG. 4b. In principle, the construction or the arrangement on the end sleeve (3) of the fiber optic light guide (3) corresponds to that of the previously described embodiment example, except that the condensing optical element (21') is now made as a spherical lens.

The distance (d') between the entry side boundary surface of the spherical lens and the exit plane of the fiber optic light guide (2) has to be dimensioned corresponding to the optical properties of the condensing element used, in order to ensure that the applied laser radiation is focused in the ciliary body of the eye on contact of the sleeve portion (20') or of the condensing optical element (21') with the surface of the eye. In an advantageous embodiment, the distance d' again amounts to 2–12 mm, preferably 6 mm, and the spherical lens is made of KF9 glass and has a spherical radius of 0.5–3 mm, preferably r=1.5 mm. However, sapphire or ruby spherical lenses are also suitable, which can be obtained with high precision and in large numbers, and therefore relatively inexpensively.

In embodiments with a convex distal surface of the optical element, the additional advantage arises that transient slight pressure traces remain on the subject's eye after the application. Already treated places can hence be recognized during the treatment, and a double treatment of the same place can be avoided.

In an embodiment of the sleeve portion as a disposable article, it has been found to be advantageous to make this as a plastic injection molded part. Thus it is even possible to make the condensing optical element likewise as an integrated injection molded part. As a possible material for this, for example, PMMA (polymethyl methacrylate) is used.

When the sleeve portion is used a number of times, attention must be paid to selecting for it a sterilizable, preferably autoclavable, material. Accordingly only the sleeve portion has to be sterilized after use, since only this portion comes into contact with the eye being treated. Suitable materials for this are, for example, aluminum or polysulfone. The optical element is then a part which is separately arranged in the sleeve portion.

Because of the simple interchangeability of the sleeve portion in the applicator according to the invention, it is further advantageous to keep in readiness several such sleeve portions in which there are provided condensing optical elements having different optical and/or geometric dimensions. It is then possible, without problems, to match very varied ocular geometries.

In an advantageous apparatus for treatment of excessively high internal ocular pressure by means of the applicator according to the invention, a diode laser is provided on the coupling-in side, its radiation being coupled into a fiber optic light guide and applied to the eye by means of the applicator according to the invention. A laser wavelength of 790–830 nm has been found to be advantageous here. However, a Nd:YAG laser with a wavelength of 1,064 nm can also be used.

We claim:

1. Applicator for treatment of an elevated internal ocular pressure by means of laser radiation, comprising:
   a fiber optic light guide (2), having an exit side with an exit surface at one end,
   a sleeve portion (4, 20, 20') releasably connected to said end of said light guide (2) on said exit side,
   an optical element (21, 21') arranged on said sleeve portion (4, 20, 20') at a first distance from said exit surface of said light guide (2),
   a handpiece (1) surrounding said light guide (2) on said exit side at a second distance from said exit surface of said light guide (2), and
   manipulation of said handpiece causing adjustment of said second distance, wherein said second distance between said handpiece (1) and said exit surface of said light guide (2) is adjustable without altering said first distance between said optical element (21, 21') and said exit surface of said light guide (2).

2. Applicator according to claim 1, wherein said optical element (21, 21') is dimensioned and arranged in said sleeve portion (4, 20, 20'), for focusing said laser radiation in a ciliary body of an eye on contact of said sleeve portion (4, 20, 20') with a surface of said eye.

3. Applicator according to claim 1, wherein said handpiece (1) has a securing device (10a–10d, 6) to releasably receive said light guide (2).

4. Applicator according to claim 3, wherein said securing device (10a–10b, 6) is constructed according to a collet chuck principle, releasably surrounds an end sleeve (3) on said light guide (2), and provides a variable setting of said second distance between said handpiece (1) and said exit surface of said light guide (2).

5. Applicator according to claim 1, wherein said handpiece (1) is made of material selected from aluminum, stainless steel, and hard plastics.

6. Applicator according to claim 1, wherein said light guide (2) has an end sleeve (3) thereon, and said sleeve portion (4, 20, 20') and said end sleeve (3) are dimensioned and arranged for slipping movement of said sleeve portion (4, 20, 20') on said end sleeve (3).

7. Applicator according to claim 2, wherein said optical element (21') comprises a spherical lens (21') arranged in said sleeve portion (20').

8. Applicator according to claim 2, wherein said optical element (21) comprises a plano-convex lens (21) arranged in said sleeve portion (20).

9. Applicator according to claim 1, wherein said sleeve portion (4, 20, 20') and said optical element (21, 21') comprise an integrally injection molded part.

10. Applicator according to claim 1, wherein said sleeve portion (4, 20, 20') is made of material selected from PMMA, aluminum and polysulfone.

11. Applicator according to claim 7, wherein said spherical lens is made of KF9 glass, has a radius of 0.5–3 mm, and is arranged in said sleeve portion (20') at a distance from said exit surface of said light guide (2) corresponding to four times said radius.

12. Applicator according to claim 1, wherein said optical element (21, 21') has an exit surface and is arranged in said sleeve portion (20, 20') such that said exit surface provides a contact surface with the surface of the eye.

13. Applicator according to claim 1, wherein said sleeve portion (4, 20, 20') has an interior surface forming a stop (22, 22') for contacting end sleeve (3) on said light guide (2) for providing a defined and reproducible relative position between said exit surface of said light guide and said optical element (21, 21').

14. Apparatus for treatment of an elevated internal ocular pressure by means of laser radiation comprising an applicator according to claim 1 in combination with a diode laser coupled to said fiber optic light guide (2) of said applicator.

15. Apparatus according to claim 14, in which laser radiation supplied by said diode laser has a wavelength of 790–830 nm.

* * * * *